United States Patent [19]

Gabrielsen et al.

[11] 4,368,246

[45] Jan. 11, 1983

[54] PHOTOGRAPHIC MATERIALS AND PROCESSES COMPRISING COLOR-FORMING SULFONAMIDODIPHENYLAMINE DYE PRECURSORS AND CORRESPONDING PHENAZINE DYES

[75] Inventors: Rolf S. Gabrielsen, Webster; Patricia A. Graham, Williamson; James E. Klijanowicz, Pittsford, all of N.Y.

[73] Assignee: Eastman Kodak Company, Rochester, N.Y.

[21] Appl. No.: 280,673

[22] Filed: Jul. 6, 1981

[51] Int. Cl.$^3$ .............................. 430 955; G03C 7/00; G03C 1/40

[52] U.S. Cl. ....................................... 430/9; 430/364; 430/375; 430/440; 430/448; 430/461; 430/483; 430/542

[58] Field of Search .................. 430/9, 364, 375, 542, 430/955, 17, 440, 448, 461, 483

[56] References Cited

U.S. PATENT DOCUMENTS

| | | | |
|---|---|---|---|
| 3,482,971 | 12/1969 | Bloom et al. | 96/3 |
| 3,498,785 | 3/1970 | Bloom et al. | 96/3 |
| 3,622,603 | 11/1971 | Bloom et al. | 260/397.7 |
| 3,658,524 | 4/1972 | Piesach | 96/3 |
| 3,813,244 | 5/1974 | Villard | 430/17 |
| 3,938,995 | 2/1976 | Gompf et al. | 96/55 |
| 4,110,355 | 8/1978 | Bloom | 260/372 |

OTHER PUBLICATIONS

*Research Disclosure*, Dec., 1978, Item No. 17643, Jun., 1978, Item No. 17029.

*Primary Examiner*—J. Travis Brown
*Attorney, Agent, or Firm*—Richard E. Knapp

[57] ABSTRACT

In a photographic material for producing a dye image or a dye image and silver image comprising (1) a photographic metal salt, such as photographic silver halide, and (2) a dye precursor, improved images are provided by means of a color-forming para-sulfonamidodiphenylamine dye precursor having one to two sulfonamido groups in positions ortho to the —NH— moiety separating the two phenyl groups of the sulfonamidodiphenylamine and wherein the sulfonamidodiphenylamine, in oxidized form, intramolecularly reacts to produce a sulfonamido-substituted phenazine dye. An exposed photographic material containing the color-forming sulfonamidodiphenylamine dye precursor is processed to produce a negative phenazine dye-enhanced silver image. Alternatively, the exposed photographic material is processed to produce a positive phenazine dye image.

44 Claims, No Drawings

PHOTOGRAPHIC MATERIALS AND PROCESSES COMPRISING COLOR-FORMING SULFONAMIDODIPHENYLAMINE DYE PRECURSORS AND CORRESPONDING PHENAZINE DYES

FIELD OF THE INVENTION

This invention relates to a photographic material and process for producing a dye image and silver image by means of photosensitive silver halide and a color-forming para-sulfonamidodiphenylamine dye precursor which, in oxidized form, intramolecularly reacts to produce a sulfonamido-substituted phenazine dye. One aspect of the invention relates to a photographic element for producing such a dye enhanced silver image by means of the dye precursor. Another aspect of the invention relates to a photographic composition comprising the color-forming sulfonamidodiphenylamine dye precursor or the corresponding phenazine dye. A further aspect of the invention relates to a process for producing a negative, dye enhanced silver image in an imagewise exposed photographic element by developing the element according to the invention in an alkaline cross-oxidizing photographic developer solution to produce a phenazine dye enhanced silver image. A further aspect of the invention relates to producing a positive phenazine dye image in a photographic element according to the invention.

DESCRIPTION OF THE STATE OF THE ART

Photographic materials for producing silver and dye images are well known. It has been desirable to provide alternative means for producing a dye image, especially a dye image that enhances a silver image, other than by coupling reactions. Coupling reactions for forming dye images are described in, for example, U.S. Pat. No. 3,938,995. The present invention provides compounds that avoid the need for a coupling reaction to produce a dye, especially a phenazine dye, that is suitable as an image in a photographic material.

Reducing agents are known to auto react intramolecularly to form a heterocyclic ring. Such reducing agents are described in, for example, U.S. Pat. No. 3,482,971 and U.S. Pat. No. 3,622,603. The reducing agents in these patents are formed by means of a hydroxy group or amino group in the position para to an —NH— group in the compounds. The compounds of the present invention have no such hydroxy group or amino group. The compounds of U.S. Pat. No. 3,482,971 and U.S. Pat. No. 3,622,603 are not disclosed as color-providing materials, but rather as reducing agents and scavengers for oxidized reducing agents.

The term "photographic material" herein means photographic elements and photographic compositions. For instance, photographic material herein includes photographic elements and photographic compositions comprising photosensitive silver halide and a color-forming sulfonamidodiphenylamine dye precursor or phenazine dye according to the invention.

SUMMARY OF THE INVENTION

It has been found according to the invention that, in a photographic material comprising (1) a photographic metal salt, such as photosensitive silver halide, and (2) a dye precursor, improved images are provided by means of a dye precursor that comprises a color-forming para-sulfonamidodiphenylamine dye precursor having one to two sulfonamido groups in positions ortho to the —NH— moiety separating the two phenyl groups of the sulfonamidodiphenylamine and wherein the sulfonamidodiphenylamine, in oxidized form, intramolecularly reacts to produce a sulfonamido-substituted phenazine dye.

It has also been found according to the invention that a phenazine dye image is produced by a process which comprises developing an exposed photographic material according to the invention in an alkaline, cross-oxidizing, photographic silver halide developer composition to produce a phenazine dye image, preferably a phenazine dye enhanced silver image.

In each of the described photographic materials and processes, the phenazine dye in the image areas has desired stability.

DETAILED DESCRIPTION OF THE INVENTION

Many color-forming para-sulfonamidodiphenylamine dye precursors are useful in a photographic material and process according to the invention. Combinations of color-forming para-sulfonamidodiphenylamine dye precursors are useful, if desired. Illustrative color-forming sulfonamidodiphenylamine dye precursors consist essentially of compounds represented by the formula:

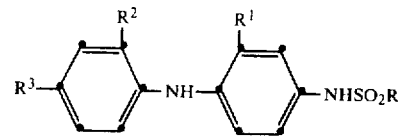

wherein:
- R is alkyl containing 1 to 20 carbon atoms, such as methyl, ethyl, propyl, butyl, decyl and eicosyl, aryl containing 6 to 20 carbon atoms, such as phenyl, para-tolyl and 2,4,6-triisopropylphenyl, or alkaryl containing 7 to 20 carbon atoms, such as benzyl and xylyl;
- $R^1$ and $R^2$ are individually hydrogen, alkyl containing 1 to 4 carbon atoms, such as methyl, ethyl, propyl or butyl, or —NHSO$_2$R$^4$; and at least one of $R^1$ and $R^2$ is —NHSO$_2$R$^4$;
- $R^3$ is alkoxy containing 1 to 20 carbon atoms, such as methoxy, ethoxy, propoxy and butoxy, alkyl containing 1 to 20 carbon atoms, such as methyl, ethyl, propyl, decyl and eicosyl, or

- $R^4$ is alkyl containing 1 to 20 carbon atoms, such as methyl, ethyl, propyl, butyl, decyl and eicosyl, aryl containing 6 to 20 carbon atoms, such as phenyl, para-tolyl and 2,4,6-triisopropylphenyl, or alkaryl containing 7 to 20 carbon atoms, such as benzyl and xylyl;
- $R^5$ is hydrogen or alkyl containing 1 to 20 carbon atoms, such as methyl, ethyl, propyl, butyl, decyl and eicosyl; and
- $R^6$ is alkyl containing 1 to 20 carbon atoms, such as methyl, ethyl, propyl, butyl, decyl and eicosyl.

The sulfonamidodiphenylamine dye precursor is capable, in oxidized form, of intramolecular reaction to produce a sulfonamido-substituted phenazine dye. The terms "alkyl" and "aryl" herein are intended to include unsubstituted alkyl, such as unsubstituted methyl, ethyl, propyl or butyl, and unsubstituted aryl, such as unsubstituted phenyl. The terms also include alkyl and aryl that are substituted by groups which do not adversely affect the desired properties of the photographic material or the sulfonamidodiphenylamines. Examples of useful substituted alkyl groups include alkyl substituted by alkoxy, carboxamidomethoxy or methylsulfonamido. The methylsulfonamido and methanesulfonamido groups herein are synonymous. Examples of useful substituted aryl include methoxyphenyl, 2,4,6-triisopropylphenyl and tolyl. The 2,4,6-triisopropylphenyl and 2,4,6-triisopropylbenzene groups herein are synonymous.

An optimum color-forming sulfonamidodiphenylamine dye precursor according to the invention will depend upon such factors as the desired image, particular photographic material, processing steps and conditions, particular photosensitive silver halide in the photographic material, other components in the photographic material, and the particular cross-oxidizing developer. Examples of useful color-forming sulfonamidodiphenylamines according to the invention include the following:

thyl)-N-ethyl]aminodiphenylamine represented by the formula:

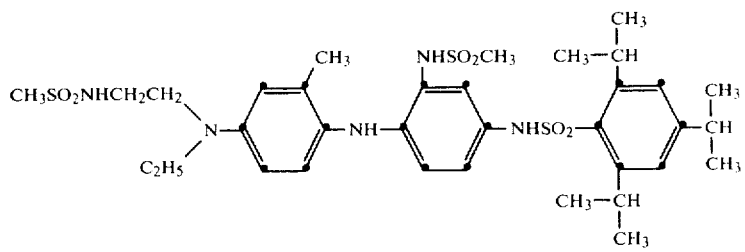

2'-Methylsulfonamido-4'-(2,4,6-triisopropylphenyl)-sulfonamido-4-(hydroxytrisethoxy)diphenylamine represented by the formula:

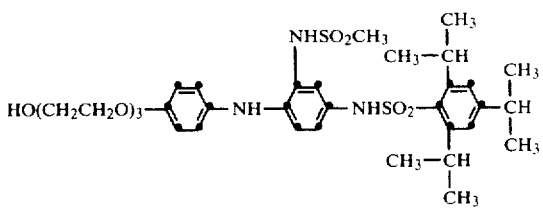

2,4'-Bis(methylsulfonamido)-4-N,N-diethylamino diphenylamine represented by the formula:

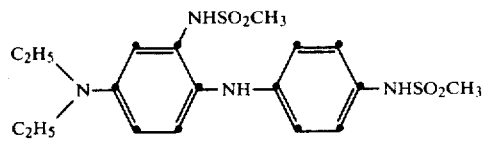

4-[N-(β-Methanesulfonamidoethyl)N-ethyl]amino-2-methyl-2',4'-bis(2,4,6-triisopropylphenyl)sulfonamido diphenylamine represented by the formula:

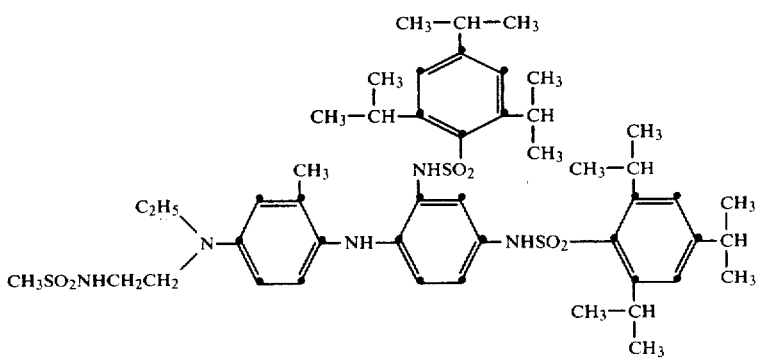

2,4-Bis(methylsulfonamido)-4'-N,N-diethylaminodi phenylamine represented by the formula:

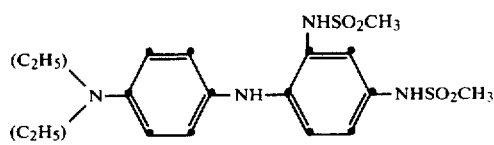

2'-Methylsulfonamido-4'-(2,4,6-triisopropylphenyl)-sulfonamido 2-methyl-4-[N-(2-methanesulfonamidoe- 4-n-Hexyloxy-2'-methanesulfonamido-4'-(2,4,6-triisopropylphenyl)sulfonamido diphenylamine represented by the formula:

4-n-Hexyl-2'-methanesulfonamido-4'-(2,4,6-triisopropylphenyl)sulfonamido diphenylamine represented by the formula:

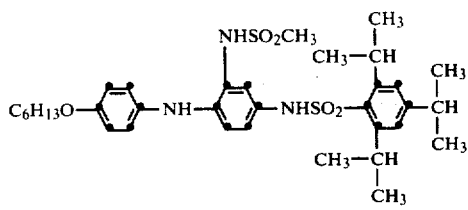

4-Methoxy-2'-methanesulfonamido-4'-(2,4,6-triisopropylphenyl)sulfonamido diphenylamine represented by the formula:

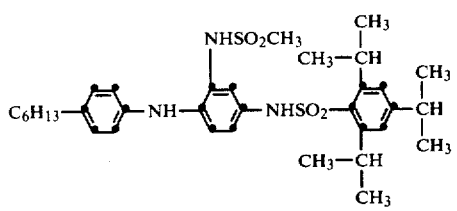

Each of the listed color-forming sulfonamidodiphenylamine dye precursors forms a corresponding phenazine dye by intramolecular reaction following oxidation.

The color-forming sulfonamidodiphenylamine dye precursors are prepared by a series of steps. The first step involves reaction of an appropriate nitrofluorosulfonamido compound with an appropriate phenylenediamine in the presence of a suitable solvent, such as α-picoline to produce an appropriate nitro-substituted sulfonamidodiphenylamine with the release of hydrogen fluoride. The second step involves hydrogenation in the presence of a suitable catalyst, such as Raney nickel, of the nitrosubstituted sulfonamidodiphenylamine to produce an amino compound. The amino compound is reacted with an appropriate sulfonyl chloride in the presence of a suitable solvent, such as pyridine, to produce the desired sulfonamidodiphenylamine dye precursor according to the invention.

The preparation of 4-N,N-diethylamino-2',4'-bismethanesulfonamidodiphenylamine is illustrative of the method of preparing a color-forming sulfonamidodiphenylamine dye precursor according to the invention. This preparation is as follows:

The following reaction was carried out:

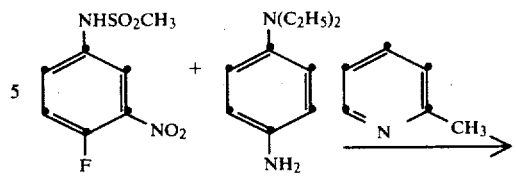

The solution of 42.1 g (0.1 mole) of the nitro compound and 29.5 g (0.18 mole) of the paraphenylenediamine compound in 250 ml of α-picoline was refluxed overnight under nitrogen. The mixture was then poured over ice, and after the ice had melted, the composition was filtered. The collected solid was washed with water until clear washings were obtained and air dried. The desired intermediate was recrystallized from ethyl acetate to provide a red solid having a melting point of 168° to 170° C. This intermediate was identified by elemental analysis.

Then the following reaction was carried out:

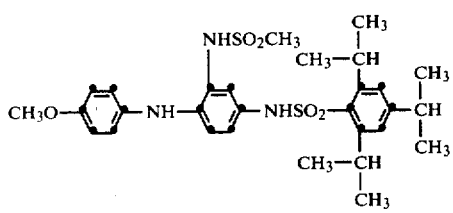

A solution of 20 g (0.053 mole) of the described nitro-substituted sulfonamidodiphenylamine in 400 ml of degassed tetrahydrofuran was reduced over Raney nickel (catalyst) at room temperature at 40 psi of hydrogen. The catalyst was removed by filtration and the filtrate concentrated to dryness under nitrogen to protect the reaction mixture against air oxidation. A dark blue gum was obtained. This was dissolved in 250 ml of pyridine and treated with methanesulfonyl chloride.

After stirring overnight at room temperature, the solution was poured into 2 liters of water and extracted twice with ethyl acetate. The extracts were combined, washed 5 times with water and dried over magnesium sulfate. After concentration to dryness, a deep red gum that had an odor of pyridine was obtained. This was dissolved in 75 ml of toluene and titrated with about 125 ml of ligroin, whereupon a product gummed out on the sides of the flask. After adding another 200 ml of ligroin, scratching the gum and vigorous stirring, solidification began. A dark rose colored solid was collected. The solid was dissolved in 100 ml of ethyl acetate, washed with water, and dried over magnesium sulfate. Concentration to dryness of the resulting mixture yielded a bright red glass. Thin layer chromatography indicated one major air sensitive component, some magenta dye, and several minor impurities. The product was recrystallized twice from 100 ml of toluene containing a trace of ethyl acetate to effect complete solution. A very pale pink solid was produced having a melting point of 135° C. to 137° C. The desired product was identified by mass spectrographic analysis and nuclear magnetic resonance analysis, as well as elemental analysis.

A corresponding sulfonamido-substituted phenazine dye is produced from the color-forming sulfonamidodiphenylamine dye precursor by intramolecular reaction following oxidation by an oxidizing agent. This is effected by means of a suitable oxidizing agent, such as an oxidized cross-oxidizing developing agent, for example an oxidized 3-pyrazolidone cross-oxidizing developing agent.

The hue of the phenazine dye produced from the color-forming sulfonamidodiphenylamine dye precursor varies, depending upon such factors as the particular groups on the dye precursor, processing conditions, and other components in the photographic material. Generally, the dye precursor is colorless in the photographic material prior to processing. Some of the dye precursors have a slight yellow color in the photographic material. This slight color is not considered unacceptable.

The term "colorless" herein means that the dye precursor according to the invention does not absorb radiation to an undesired degree in the visible region of the electromagnetic spectrum. In some photographic materials, the dye precursor according to the invention absorbs radiation at certain areas of the electromagnetic spectrum which does not adversely affect the desired properties of the photographic material or the desired image formed upon processing.

Most of the color-forming sulfonamidodiphenylamine dye precursors according to the invention in the photographic material absorb electromagnetic radiation outside the visible region of the electromagnetic spectrum before imagewise exposure and processing of the photographic material. The nature of the absorption and degree of absorption of the dye precursor according to the invention depends upon the nature of the substituent groups on the dye precursor.

The photographic materials according to the invention comprise a photographic metal salt, preferably a photographic silver salt such as photographic silver halide. It is essential that the photographic metal salt not adversely affect the desired imaging process, such as the intramolecular reaction that occurs in the photographic material. Examples of useful photographic silver halides are silver chloride, silver bromide, silver bromoiodide, silver, chlorobromoiodide, silver iodide and mixtures thereof. The photographic silver halide is generally present in the photographic material in the form of an emulsion which is a dispersion of the photographic silver halide in a suitable binder. The photographic silver halide is present in a range of grain sizes from fine grain to coarse grain. The composition containing the photographic silver halide is prepared by any of the well known procedures in the photographic art, such as described in *Research Disclosure*, December 1978, Item No. 17643. The photographic silver halide material contains addenda commonly used in photographic silver halide materials, such as chemical sensitizers, brighteners, antifoggants, emulsion stabilizers, light absorbing or scattering materials, hardeners, coating aids, plasticizers, lubricants and antistatic materials, matting agents, development modifiers and other addenda described in *Research Disclosure*, December 1978, Item No. 17643.

The photographic silver halide is generally spectrally sensitized by means of spectrally sensitizing dyes, as described in *Research Disclosure*, December 1978, Item No. 17643. Spectral sensitizing dyes which are useful in the photographic materials of the invention include polymethine sensitizing dyes which include the cyanines, merocyanines, complex cyanines and merocyanines (including tri, tetra and polynuclear cyanines and merocyanines), as well as oxonols, hemioxonols, styryls, merostyryls and streptocyanines. Combinations of spectral sensitizing dyes are useful.

A range of concentrations of photographic silver halide is present in the photographic material according to the invention. An optimum concentration of photographic silver halide will depend upon such factors as the desired image, processing conditions, particular dye precursor according to the invention, other components in the photographic material, and particular cross-oxidizing reducing agent in the photographic material. A useful concentration of photographic silver halide in the photographic material according to the invention is within the range of about 1 mole to about 10 moles of photographic silver halide per mole of dye precursor according to the invention in the photographic material. The coverage of photographic silver halide is less than otherwise might be useful, due to the enhancing properties of the phenazine dye produced upon processing of the photographic material.

The color-forming sulfonamidodiphenylamine dye precursor according to the invention is in any suitable location in the photographic material which produces the desired phenazine dye upon processing. The color-forming sulfonamidodiphenylamine dye precursor should be in a location with respect to the photographic silver halide which produces the desired phenazine dye image and the desired silver image upon processing. According to the invention, the color-forming sulfonamidodiphenylamine dye precursor is in a location with respect to the photographic silver halide that produces a dye image and silver image upon appropriate processing. If desired, a proportion of the sulfonamidodiphenylamine dye precursor is in a layer contiguous to the layer of the photographic element comprising photographic silver halide. The term "in reactive association" herein means that the photographic silver halide and the color-forming sulfonamidodiphenylamine dye precursor are in a location with respect to each other which enables the photographic material upon processing to produce a desired dye image and a desired silver image. Many developing agents are useful for developing an image in a photographic material according to the invention. Silver halide developing compositions are useful according to the invention, provided the compositions comprise a cross-oxidizing developing agent which will cross-oxidize with the color-forming sulfonamidodiphenylamine dye precursor according to the invention. Such a developer, specified herein as a cross-oxidizing developer, becomes oxidized during development by reducing exposed silver halide to silver metal. The oxidized developer then cross-oxidizes the color-forming sulfonamidodiphenylamine dye precursor to form the desired phenazine dye.

A cross-oxidizing developing agent (COD) enables the color-forming sulfonamidodiphenylamine dye precursor to become oxidized without the sulfonamidodiphenylamine itself developing silver. The cross-oxidizing developing agent is alternatively viewed as an electron transfer agent which shuttles electrons between the developing silver halide and the sulfonamidodiphenylamine.

The sulfonamidodiphenylamine is frequently in an oil phase in order to aid dispersion in a layer of a photographic element.

The requirements for a cross-oxidizing developing agent in the most general cases are: (a) the developing agent must have sufficient electrochemical potential under the conditions of use to develop exposed silver halide; (b) in its oxidized form, the developing agent must be of such electrochemical potential as to oxidize the sulfonamidodiphenylamine; and (c) in its oxidized form, the developing agent must be stable to decomposition by other chemical reactions for a sufficient time to undergo the redox reaction with the sulfonamidodiphenylamine. If one or more of these conditions is not met, the developing agent is not a cross-oxidizing developing agent. Whether a particular developing agent meets the requirements of a cross-oxidizing developing agent depends upon the conditions under which development occurs, other components in the developing composition, the pH of the developing composition, the temperature of the development process, and the length of development time. Developing agents which meet the requirements of a cross-oxidizing developing agent under development conditions are useful. Especially useful examples of developing agents that are cross-oxidizing developing agents are 3-pyrazolidone developing agents, such as 1-phenyl-3-pyrazolidone, 1-phenyl-4,4-dimethyl-3-pyrazolidone and 4-hydroxymethyl-4-methyl-1-phenyl-3-pyrazolidone. Such cross-oxidizing developing agents are described in, for example, U.S. Pat. No. 3,938,995. Combinations of developing agents are also useful, if desired. Combinations of non-cross-oxidizing developing agents and cross-oxidizing developing agents are useful. The concentration of non-cross-oxidizing developing agent in the combination should be a minor proportion of the total combination, such as less than about 10 percent by weight of the total combination. Examples of combinations of a non-cross-oxidizing developing agent in a cross-oxidizing developing agent include the combination of 4-hydroxymethyl-4-methyl-1-phenyl-3-pyrazolidone with a minor proportion of at least one of the non-cross-oxidizing developing agents:ascorbic acid, hydroquinone and pyrimidine. Selection of an optimum silver halide developing agent or developing agent combination depends upon the desired image, the particular photosensitive silver halide, processing conditions, the particular color-forming sulfonamidodiphenylamine dye precursor, the pH of the developing composition, the temperature of the development process and the length of development time.

The silver halide developing agent or developing agent combination is alternatively incorporated in the photographic material. Generally, the developing agent is most useful in a processing solution or in a processing solution and incorporated in the photographic element to produce a desired phenazine dye image and silver image.

The cross-oxidizing developing agent is useful in a range of concentrations in the photographic material or in a processing composition in which the photographic material is processed. A useful concentration of developing agent when the developing agent is present in the photographic material is within the range of about 0.1 to about 1.0 mole of developing agent per mole of color-forming sulfonamidodiphenylamine dye precursor in the photographic material. A useful concentration of developing agent in the processing solution for processing a photographic material containing a color-forming sulfonamidodiphenylamine dye precursor according to the invention is within the range of about 0.5 to about 2 g of developing agent per liter of processing solution.

The term "developing agent" herein includes compounds which are developing agents and developing agent precursors. That is, those compounds are included which are not developing agents in the photographic material until a condition occurs, such as contact with a suitable activator for the photographic material.

The tone of the silver image and dye image produced in a photographic material according to the invention varies, depending upon such factors as the silver morphology of the developed silver image, the covering power of the silver materials, the particular phenazine dye formed, the particular developing agent, processing conditions, and concentration of components. In photographic materials according to the invention that provide a brown silver image, a phenazine dye produced from the described color-forming sulfonamidodiphenylamine dye precursor is especially useful which is complementary in hue to the silver image.

The photographic materials according to the invention generally comprise a binder. Binders are useful alone or in combination in a photographic material according to the invention. Useful binders include both naturally occurring substances such as proteins, for example, gelatin, gelatin derivatives, cellulose derivatives, polysaccharides such as dextran, gum arabic and the like; and synthetic polymeric materials such as water soluble polyvinyl compounds like polyvinyl pyrrolidone and acrylamide polymers.

If desired, the photographic elements according to the invention contain an overcoat layer and/or interlayer and/or subbing layer to provide desired properties. The overcoat layer, for example, increases resistance to abrasion and other markings on the element. The overcoat layer, interlayer or subbing layer contain, alone or in combination, vehicles and binders that are useful in the layer of the element containing the photosensitive silver halide. Gelatin is an especially useful binder.

A photographic element according to the invention comprises a variety of supports. Useful supports include those which are resistant to adverse changes in structure due to processing conditions and which do not adversely affect the desired sensitometric properties of the photographic materials. Useful supports include cellulose ester, poly(vinyl acetal), poly(ethylene terephthalate) and polycarbonate films, as well as related films and resinous materials. Glass, paper, metal and the like supports are also useful. A flexible support is generally most useful.

In preparing a photographic material comprising the color-forming sulfonamidodiphenylamine dye precursor according to the invention, a dispersion solvent is generally useful to produce a coating composition. A coupler solvent known in the photographic art is generally most useful for aiding dispersion of the sulfonamidodiphenylamine dye precursor. Examples of useful coupler solvents include N-n-butyl acetanilide, diethyl lauramide, di-n-butyl phthalate and 2,4-ditertiaryamylphenol. The sulfonamidodiphenylamine dye precursor is also usefully loaded into a latex, or a non-solvent dispersion is prepared, if desired.

Photographic materials according to the invention are coated on a suitable support by procedures known in the photographic art. Such procedures include, for example, immersion or dip coating, roller coating, reverse roll coating, air knife coating, doctor blade coating, spray coating, extrusion coating, bead coating, stretch flow coating and curtain coating.

The photographic materials according to the invention are imagewise exposed by means of various forms of energy to produce a developable image. Such forms of energy include those to which the photosensitive material, especially the photosensitive silver halide, is sensitive. These forms of energy encompass the ultraviolet, visible and infrared regions of the electromagnetic spectrum, as well as electron beam and beta radiation, gamma ray, X-ray, alpha particle, neutron radiation and other forms of corpuscular wave-like radiant energy in either non-coherent (random phase) forms or coherent (in phase) forms, as produced by lasers. Exposures are monochromatic, orthochromatic or panchromatic, depending upon the spectral sensitization of the photosensitive component, especially the photosensitive silver halide. Imagewise exposure is generally for a sufficient time and intensity to produce a developable latent image in the photographic material.

The described photographic elements according to the invention are processed in a process which produces a negative dye image and silver image in the photographic element. The photosensitive silver halide contained in the photographic element according to the invention is generally processed following exposure by associating the silver halide with an aqueous alkaline medium in the presence of a suitable cross-oxidizing developing agent contained in the medium or the element according to the invention.

If a reversal phenazine dye image is desired in the photographic element according to the invention, a process is most useful in which a non-cross-oxidizing developing composition is used for processing the exposed element as a first development step. During this step, the exposed silver halide is reduced to elemental silver by the non-cross-oxidizing developing composition. The non-cross-oxidizing developing composition does not, when oxidized, oxidize the color-forming sulfonamidodiphenylamine dye precursor to its corresponding phenazine dye.

The non-cross-oxidizing developer compositions useful in this step are generally alkaline solutions comprising a non-cross-oxidizing developing agent. Non-cross-oxidizing developing agents are well known in the photographic art and include many silver halide developing agents which will reduce exposed silver halide to silver, but will not oxidize the color-forming sulfonamidodiphenylamine to a corresponding phenazine dye.

In a second step of the process for forming a reversal dye image, fogging is accomplished by exposing the photographic element to light or by chemical fogging by means of fogging compositions known in the photographic art.

Following the fogging step, a second silver halide developing step is carried out. This is carried out by means of a cross-oxidizing developing composition. It is in this step that the phenazine dye image is formed. Any silver halide developing composition is useful in this step, provided that it cross-oxidizes the color-forming sulfonamidodiphenylamine dye precursor to a desired phenazine dye. Such silver halide developing compositions include an alkaline solution comprising a cross-oxidizing silver halide developing agent. This cross-oxidizing developing agent becomes oxidized during development by reducing exposed or fogged silver halide to silver metal. Oxidized developer then cross-oxidizes the color-forming sulfonamidodiphenylamine dye precursor to produce a desired phenazine dye. A positive phenazine dye image is formed which is also described herein as a reversal dye image.

The color-forming sulfonamidodiphenylamine dye precursor according to the invention is also usefully incorporated in a photothermographic material, such as a photothermographic silver halide material. Photothermographic materials in which the sulfonamidodiphenylamine dye precursor are incorporated are described in, for example, *Research Disclosure*, June 1978, Item No. 17029. For example, a dye image or dye and silver image is produced in a photothermographic material comprising, in binder, in reactive association: (a) a photographic silver halide, such as a photographic silver halide emulson; (b) a cross-oxidizing photographic silver halide developing agent; (c) an activating concentration of a suitable base-release agent; and (d) a color-forming sulfonamidodiphenylamine dye precursor according to the invention. The photothermographic material is generally imagewise exposed to light to provide a developable latent image which is then developed by merely uniformly heating the photothermographic element to processing temperature, such as a temperature within the range of about 100° C. to about 180° C. This also enables formation of the desired phenazine dye. Another form of photothermographic material comprises, in binder, in reactive association: (a) photographic silver halide, which is formed in situ or ex situ; (b) an oxidation reduction image forming combination comprising: (i) an organic metal salt oxidizing agent, especially a silver salt of a fatty acid, such as silver behenate, silver laurate or silver stearate, with (ii) an organic cross-oxidizing reducing agent for the oxidizing agent, such as a 3-pyrazolidone reducing agent; and (c) a color-forming sulfonamidodiphenylamine dye precursor as described. This photothermographic material is also imagewise exposed to light and then uniformly heated to provide a silver image and phenazine dye image.

An advantage of the described phenazine dyes in a photographic material according to the invention is that the dyes provide satisfactory stability to post-processing conditions and visible light exposure. A simple test is useful for establishing the degree of stability which is desired for a phenazine dye image produced from a color-forming sulfonamidodiphenylamine dye precursor according to the invention. One such test is a test known in the photographic art in which the processed photographic element is exposed to a Simulated Average North American Skylight (SANS) with continuous 5,400 LUX of exposure at an average temperature of 21° C. at 45 percent relative humidity. A comparison of the stability of the tested phenazine dye is then observed.

The color-forming sulfonamidodiphenylamine dye precursor is, in one embodiment of the invention, incorporated in a photographic silver halide processing composition for producing a dye enhanced silver image. Such a processing composition comprises a cross-oxidizing photographic silver halide developing agent and the desired color-forming sulfonamidodiphenylamine dye precursor or a combination of such dye precursors. The photographic processing composition is, for example, a silver halide developing composition, a hardener composition or a stabilizing composition. The processing composition generally comprises a base or base-release agent, such as sodium hydroxide, trisodium phosphate and potassium carbonate. An example of a suitable photographic silver halide processing composition comprises a 3-pyrazolidone cross-oxidizing photographic silver halide developing agent and a color-forming sulfonamidodiphenylamine dye precursor comprising 2'-methylsulfonamido-4'-(2,4,6-triisopropylphenyl)-sulfonamido-2-methyl-4-[N-(2-methanesulfonamidoethyl)-N-ethyl]aminodiphenylamino represented by the formula:

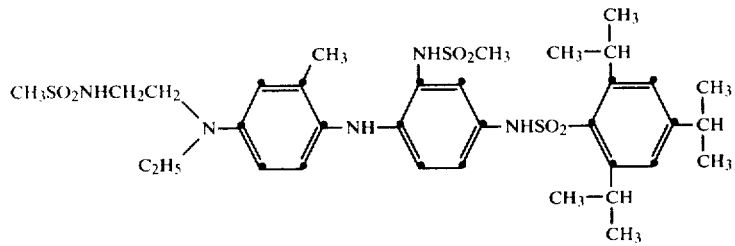

In another embodiment of the invention, the described photographic material comprises a silver halide developing agent. When a silver halide developing agent is present in the photographic material according to the invention, a developed image is produced after imagewise exposure of the photographic material by contacting the material with an alkaline activator solution which enables development of the exposed silver halide, as well as production of the desired phenazine dye.

Many alkaline activators are useful for developing an image in a photographic material according to the invention comprising an incorporated silver halide developing agent. Useful alkaline activators include those that have been found useful in the photographic art, such as in stabilization processing. Examples of useful alkaline activators include sodium hydroxide, potassium hydroxide, trisodium phosphate.12H$_2$O (pH 12), sodium metaborate (pH 12), disodium phosphate and monosodium phosphate. The optimum alkaline activator will depend upon such factors as the desired image, the particular developing agent, processing conditions, and the particular color-forming sulfonamidodiphenylamine dye precursor. An especially useful alkaline activator comprises trisodium phosphate (pH 12).

The alkaline activator is useful in a range of concentrations. A generally useful concentration of alkaline activator is within the range of about 10 to about 50 g of alkaline activator per liter of activator solution which produces a pH in the range of about 11 to about 12. An optimum concentration of alkaline activator will depend upon such factors as the particular activator, the desired image, processing conditions, particular photosensitive silver halide and particular developing agent.

Another embodiment of the invention is an exposed and processed photographic element comprising a support having thereon, in binder, a silver image enhanced by a phenazine dye image comprising a phenazine dye represented by the formula:

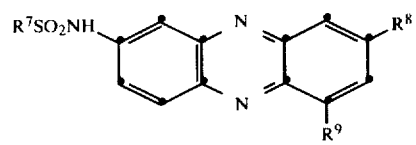

wherein:
R$^7$ is alkyl containing 1 to 20 carbon atoms, such as methyl, ethyl, propyl, butyl, decyl and eisosyl, aryl containing 6 to 20 carbon atoms, such as phenyl, para-tolyl and 2,4,6-triisopropylphenyl, or alkaryl containing 7 to 20 carbon atoms, such as benzyl and xylyl;

R$^8$ is alkoxy containing 1 to 20 carbon atoms, such as methoxy, ethoxy, propoxy and butoxy, alkyl containing 1 to 20 carbon atoms, such as methyl, ethyl, propyl, decyl and eicosyl, or

R$^9$ is hydrogen, alkyl containing 1 to 4 carbon atoms, such as methyl, ethyl, propyl and butyl, or —NHSO$_2$R$^{12}$;

R$^{10}$ is hydrogen or alkyl containing 1 to 20 carbon atoms, such as methyl, ethyl, propyl, butyl, decyl and eicosyl;

R$^{11}$ is alkyl containing 1 to 20 carbon atoms, such as methyl, ethyl, propyl, butyl, decyl and eicosyl; and, R$^{12}$ is alkyl containing 1 to 20 carbon atoms, such as methyl, ethyl, propyl, butyl, decyl and eicosyl, aryl containing 6 to 20 carbon atoms, such as phenyl, para-tolyl and 2,4,6-triisopropyl, or alkaryl containing 7 to 20 carbon atoms, such as alpha-toluene.

An especially useful phenazine dye is one wherein R[7] is 2,4,6-triisopropylphenyl. This group provides very useful dye stability.

Examples of useful phenazine dyes as dye images in an exposed and processed photographic element are as follows:

2-N,N-Diethylamino-7-methanesulfonamido phenazine represented by the formula:

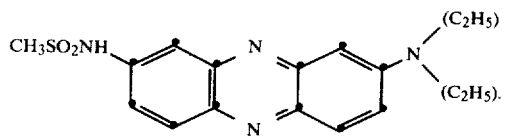

2-[N-Ethyl-N-(β-methanesulfonamidoethyl)]amino-4-methyl-7-(2,4,6-triisopropylphenyl)sulfonamido phenazine represented by the formula:

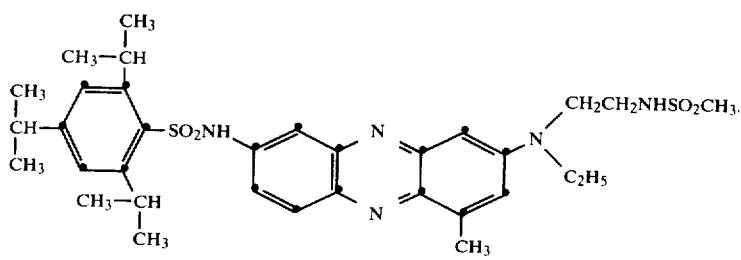

2-(Hydroxytrisethoxy)-7-(2,4,6-triisopropylphenyl)-sulfonamido phenazine represented by the formula:

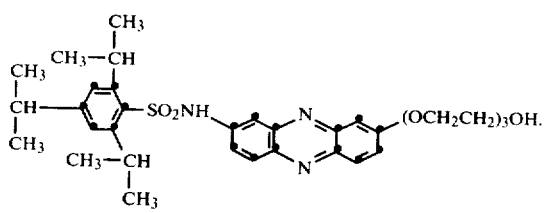

2-n-hexyloxy-7-(2,4,6-triisopropylphenyl)sulfonamido phenazine represented by the formula:

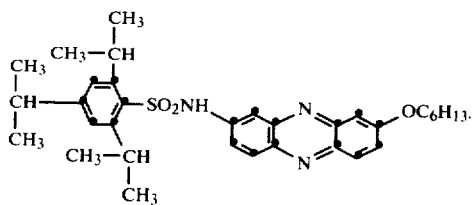

2-Methoxy-7-(2,4,6-triisopropylphenyl)sulfonamido phenazine represented by the formula:

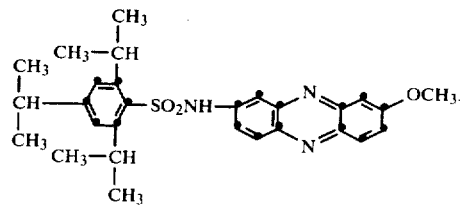

The following examples are included for a further understanding of the invention.

EXAMPLE 1

Photographic Element Containing Color-Forming Sulfonamidodiphenylamine Dye Precursor A photographic silver halide element was prepared by coating the following layer on a poly(ethylene terephthalate) film support:
- silver bromide gelatino emulsion: 9.72 mg/dm²
- gelatin (binder): 43.2 mg/dm²
- bis (vinylsulfonylmethyl)ether (gelatin hardener): 0.432 mg/dm²
- dye precursor: 13.6 mg/dm²

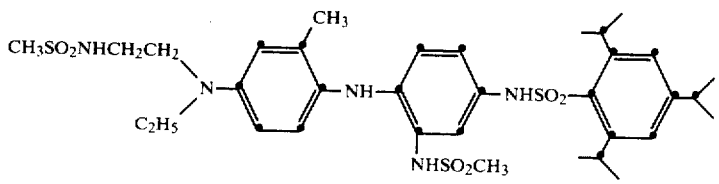

di-n-butyl phthalate (coupler 13.6 mg/dm² solvent)
The designation

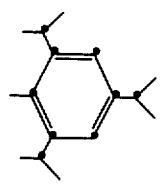

herein means a 2,4,6-triisopropylphenyl group.

The resulting photosensitive silver halide layer was permitted to dry and was then overcoated by means of a gelatin composition containing gelatin (10.8 mg/dm²) and bis (vinylsulfonylmethyl)ether (hardener) (0.108 mg/dm²). A strip of the resulting photographic film was imagewise exposed through a step tablet in a commercial sensitometer to produce a developable image in the film. Processing was carried out at 22° C. by immersing the film in a tank containing a developer composition with agitation. The developer contained the following:

Na$_3$PO$_4$.12H$_2$O: 47.5 g
4-hydroxymethyl-4-methyl-1-phenyl-3-pyrazolidone: 1.0 g
benzyl alcohol: 10.0 ml
distilled water to: 1 liter The film was immersed in the described developer for 30 seconds and then rinsed with water for 60 seconds. The film was then fixed by immersing the developed film in a fixer composition containing the following components:

Na$_2$S$_2$O$_3$.5H$_2$O: 248 g
Na$_2$CO$_3$.H$_2$O: 30 g
NaHCO$_3$: 5 g
distilled water to: 1 liter The film was fixed for 30 seconds and then washed with water for 5 minutes. The film was then permitted to air dry.

The resulting developed silver plus dye image produced a maximum density in the first step of the step tablet of 1.2 and a minimum density in the eleventh developed step from the step tablet of 0.46. An orange phenazine dye image having a maximum absorption of 471 nm was generated. This orange dye was a phenazine dye corresponding to the sulfonamidodiphenylamine dye precursor.

The phenazine dye image produced a maximum density of 0.79 to blue light.

EXAMPLE 2

Use of Another Color-Forming Sulfonamidodiphenylamine Dye Precursor

The following composition was prepared and coated as a wet coating thickness of about 100 microns on gel-subbed poly(ethylene terephthalate) film support and dried at 37.8° to 40.6° C.:

Ethylene[bis-sulfonyl acetic acid]: 0.130 g
1,3-Bis[2-S-(N,N'-ethyleneisothiourea)ethyl]urea.2-HNO$_3$: 0.078 g
2,21-Dimethyl-7,16-dioxo-2,6,8,15,17,21-hexazadocosane: 0.060 g
N,N-diethyl-3-methanesulfonamido-4'-methanesulfonamidophenylamine: 0.062 g
10% aqueous Surfactant 10G (paraisononylphenoxypolyglycidol, a trademark of and available from the Olin Corp., U.S.A.): 0.2 ml
10% aqueous gelatin: 2.5 ml
Water: 6.8 ml
Photographic Gelatino Emulsion (AgCl): 0.21 g
pH adjusted to 4.0 with KOH The resulting coating contained a total silver laydown of 3.7 mg/dm$^2$ (34 mg/ft$^2$). A sample of the coating, after incubating for eleven days at 50% relative humidity and 37.8° C., was imagewise exposed for $10^{-3}$ second in a commercial sensitometer to produce a developable latent image in the element. The exposed element was then processed by heating on a hot metal block at 160° C. until a developed image was produced. A magenta dye-enhanced silver image was produced.

EXAMPLE 3

The following gelatin-overcoated silver halide photographic element was prepared:

Overcoat

Gelatin: 10.8 mg/dm$^2$
Bis(vinylsulfonylmethyl)ether: 0.11 mg/dm$^2$

Photosensitive Layer

AgBr, 0.8μ octahedral: 9.7 (as Ag°)
Gelatin: 43.2
Bis(vinylsulfonylmethyl)ether: 0.43
N-n-butylacetanilide: 15.9
Dye Precursor: 15.9

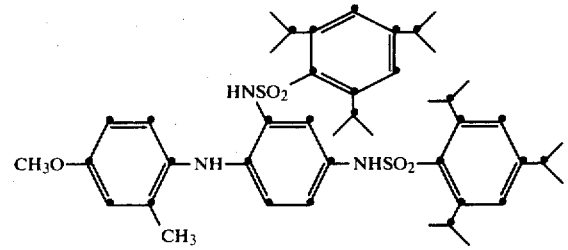

MOP herein means 4-hydroxymethyl-4-methyl-1-phenyl-3-pyrazolidone. Samples of the coating were similarly exposed. One sample was developed in a MOP developer* for 30 seconds at about 22° C. and then fixed for 30 seconds yielding a silver plus dye density ($\lambda_{max}$=470 nm) of 0.57. Another sample, similarly developed, was bleached* until cleared yielding a dye-only density ($\lambda_{max}$=470 nm) of 0.36.

| *pH-12 Phosphate buffered developer containing: | |
|---|---|
| Na$_3$PO$_4$ | 38.5 g |
| Na$_2$HPO$_4$ | 6.7 g |
| KBr | 1.0 g |
| Benzyl alcohol | 1% |
| MOP | 1.0 g |
| Water to one liter | |
| **pH-10 (NaOH adjusted) fixing solution containing: | |
| Na$_2$S$_2$O$_3$.5H$_2$O | 248.0 g |
| Na$_2$CO$_3$.H$_2$O | 30.0 g |
| NaHCO$_3$ | 5.0 g |
| Distilled water to one liter | |
| ***Bleach (similar to the composition below which is described on page 205 in British Journal of Photography Annual 1979): | |
| pH 5.9-6.1 | |
| NaFeEDTA | 100.0 g |
| KBr | 50.0 g |
| Ammonia (20%) | 6.0 ml |
| Water to one liter | |

EXAMPLE 4

The photosensitive layer differed from Example 3 in that the N-n-butylacetanilide coverage was 9.9 mg/dm$^2$ and the color-forming dye precursor, represented by the following formula:

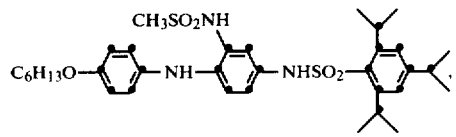

was substituted for the color-forming dye precursor of Example 3. The fixed sample had a silver plus dye density ($\lambda_{max}$ equals 510 nm) of 0.68. The fixed and bleached sample had a dye density ($\lambda_{max}$ equals 510 nm) of 0.53.

The invention has been described in detail with particular reference to preferred embodiments thereof, but it will be understood that variations and modifications can be effected within the spirit and scope of the invention.

What is claimed is:

1. In a photographic element comprising a support having thereon a photographic silver salt and a dye precursor, the improvement comprising:
as said dye precursor, a color-forming para-sulfonamidodiphenylamine having one to two sulfonamido groups in positions ortho to the —NH— moiety separating the two phenyl groups of the para-sulfonamidodiphenylamine and wherein the para-sulfonamidodiphenylamine, in oxidized form, intramolecularly reacts to produce a sulfonamido substituted phenazine dye.

2. In a photographic element comprising a support having thereon a photographic silver salt and a dye precursor, the improvement comprising:
as said dye precursor, a color-forming para-sulfonamidodiphenylamine represented by the formula:

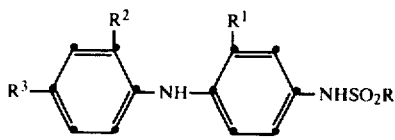

wherein:
R is alkyl containing 1 to 20 carbon atoms, aryl containing 6 to 20 carbon atoms or alkaryl containing 7 to 20 carbon atoms;
$R^1$ and $R^2$ are individually hydrogen, alkyl containing 1 to 4 carbon atoms or —NHSO$_2$R$^4$; and at least one of $R^1$ and $R^2$ is —NHSO$_2$R$^4$;
$R^3$ is alkoxy containing 1 to 20 carbon atoms, alkyl containing 1 to 20 carbon atoms or

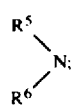

$R^4$ is alkyl containing 1 to 20 carbon atoms, aryl containing 6 to 20 carbon atoms or alkaryl containing 7 to 20 carbon atoms;
$R^5$ is hydrogen or alkyl containing 1 to 20 carbon atoms; and
$R^6$ is alkyl containing 1 to 20 carbon atoms; and, wherein the para-sulfonamidodiphenylamine has one to two sulfonamido groups in positions ortho to the —NH— moiety separating the two phenyl groups of the para-sulfonamidodiphenylamine, and,
wherein the para-sulfonamidodiphenylamine, in oxidized form, intramolecularly reacts to produce a sulfonamido substituted phenazine dye.

3. A photographic element as in claim 2 also comprising a binder.

4. A photographic element as in claim 2 wherein said photographic silver salt consists essentially of photographic silver halide.

5. A photographic element as in claim 2 wherein said color-forming para-sulfonamidodiphenylamine is represented by the formula:

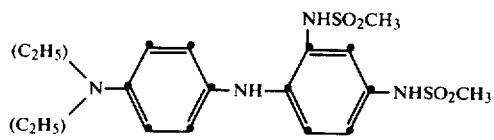

6. A photographic element as in claim 2 wherein said color-forming para-sulfonamidodiphenylamine is represented by the formula:

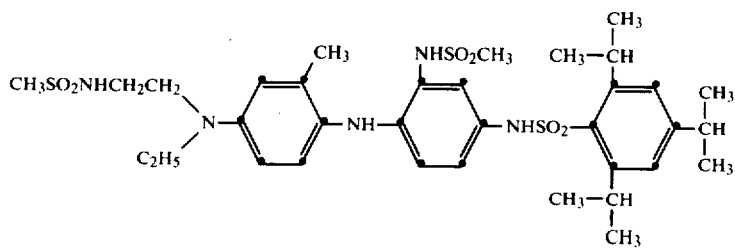

7. A photographic element as in claim 2 wherein said color-forming para-sulfonamidodiphenylamine is represented by the formula:

8. A photographic element as in claim 2 wherein said color-forming para-sulfonamidodiphenylamine is represented by the formula:

9. A photographic element as in claim 2 wherein said color-forming para-sulfonamidodiphenylamine is represented by the formula:

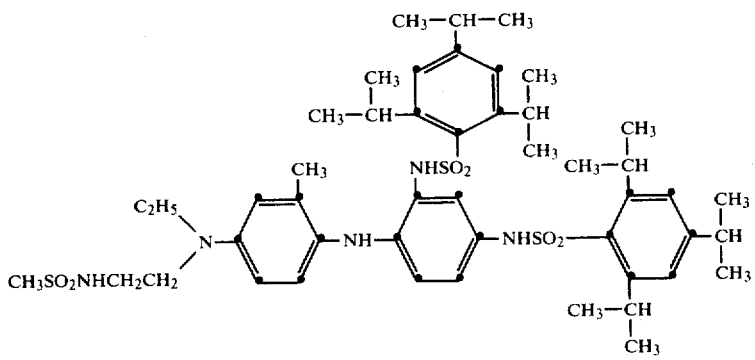

10. A photographic element as in claim 2 wherein said color-forming para-sulfonamidodiphenylamine is represented by the formula:

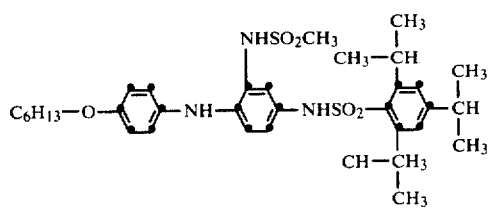

11. A photographic element as in claim 2 also comprising, in binder, in reactive association with said photographic silver salt, a cross-oxidizing, photographic silver halide developing agent.

12. A photographic element as in claim 2 also comprising, in binder, in reactive association with said photographic silver salt, a 3-pyrazolidone, photographic silver halide developing agent.

13. In a photographic element comprising a support having thereon, in a gelatino binder, in reactive association, photographic silver halide and a dye precursor, the improvement comprising:

as said dye precursor, a color-forming sulfonamidodiphenylamine represented by the formula:

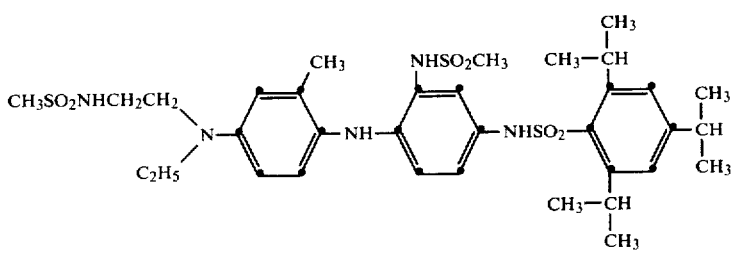

14. In a photographic composition comprising a photographic silver salt and a dye precursor, the improvement comprising: as said dye precursor, a color-forming para-sulfonamidodiphenylamine having one to two sulfonamido groups in positions ortho to the —NH— moiety separating the two phenyl groups of the para-sulfonamidodiphenylamine and wherein the para-sulfonamidodiphenylamine, in oxidized form, intramolecularly reacts to produce a sulfonamido substituted phenazine dye.

15. In a photographic composition comprising a photographic silver salt and a dye precursor, the improvement comprising:

as said dye precursor, a color-forming para-sulfonamidodiphenylamine represented by the formula:

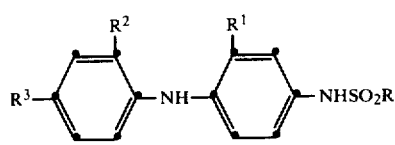

wherein:

R is alkyl containing 1 to 20 carbon atoms, aryl containing 6 to 20 carbon atoms, or alkaryl containing 7 to 20 carbon atoms;

$R^1$ and $R^2$ are individually hydrogen, alkyl containing 1 to 4 carbon atoms, or —$NHSO_2R^4$; and at least one of $R^1$ and $R^2$ is —$NHSO_2R^4$;

$R^3$ is alkoxy containing 1 to 20 carbon atoms, alkyl containing 1 to 20 carbon atoms, or

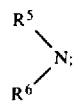

$R^4$ is alkyl containing 1 to 20 carbon atoms, aryl containing 6 to 20 carbon atoms, or alkaryl containing 7 to 20 carbon atoms;

$R^5$ is hydrogen or alkyl containing 1 to 20 carbon atoms; and $R^6$ is alkyl containing 1 to 20 carbon atoms; and, wherein the para-sulfonamidodiphenylamine has one to two sulfonamido groups in positions ortho to the —NH— moiety separating the two phenyl groups of the para-sulfonamidodiphenylamine; and, wherein the para-sulfonamidodiphenylamine, in oxidized form, intramolecularly reacts to produce a sulfonamido substituted phenazine dye.

16. A photographic composition as in claim 15 also comprising a binder.

17. A photographic composition as in claim 15 wherein said photographic silver salt is photographic silver halide.

18. A photographic composition as in claim 15 wherein said color-forming para-sulfonamidodiphenylamine is represented by the formula:

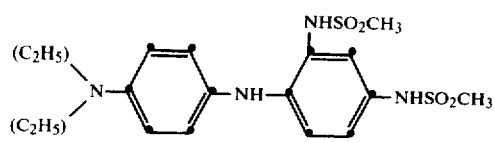

19. A photographic composition as in claim 15 wherein said color-forming para-sulfonamidodiphenylamine is represented by the formula:

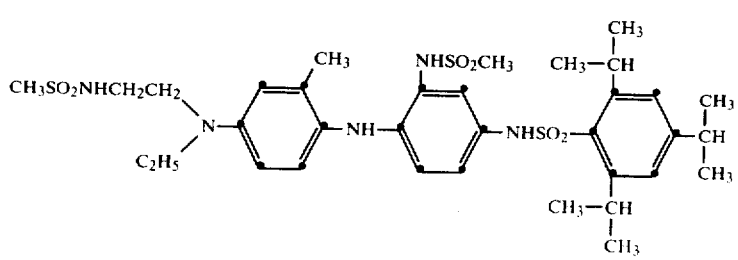

20. A photographic composition as in claim 15 wherein said color-forming para-sulfonamidodiphenylamine is represented by the formula:

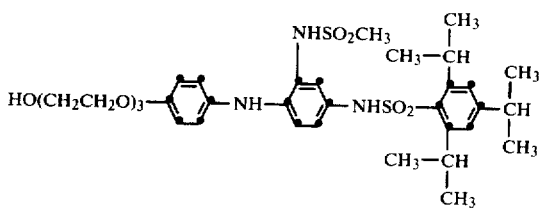

21. A photographic composition as in claim 15 wherein said color-forming para-sulfonamidodiphenylamine is represented by the formula:

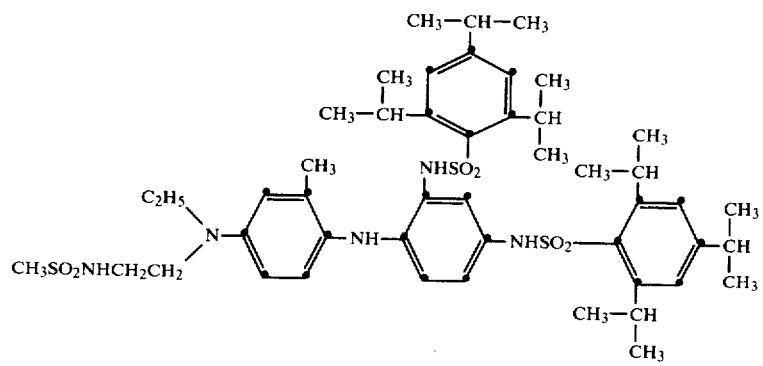

22. A photographic composition as in claim 15 wherein said color-forming para-sulfonamidodiphenylamine is represented by the formula:

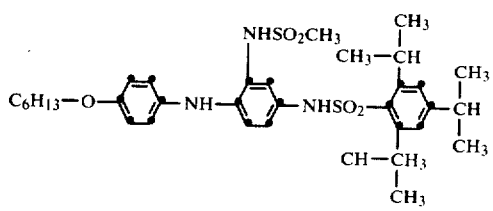

23. A photographic composition as in claim 15 wherein said color-forming para-sulfonamidodiphenylamine is represented by the formula:

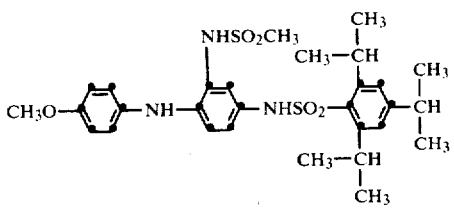

24. A photographic composition as in claim 15 also comprising, in binder, in reactive association with said photographic silver salt, a cross-oxidizing, photographic silver halide developing agent.

25. A photographic composition as in claim 15 also comprising, in binder, in reactive association with said photographic silver salt, a 3-pyrazolidone cross-oxidizing photographic silver halide developing agent.

26. In a photographic composition comprising, in a gelatino binder, photographic silver halide and a dye precursor, the improvement comprising:
   as said dye precursor, a color-forming sulfonamidodiphenylamine represented by the formula:

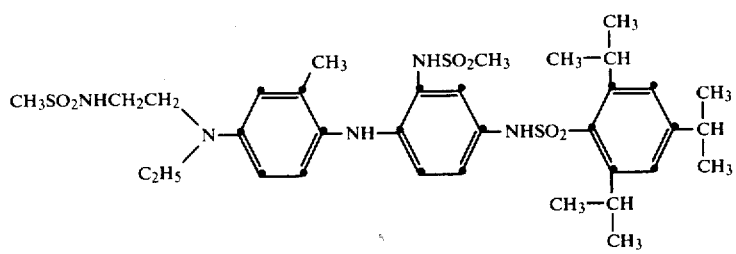

27. A method of producing a phenazine dye enhanced silver image in an exposed photographic element comprising a support having thereon, in reactive association, a photographic silver salt and a dye precursor comprising a color-forming para-sulfonamidodiphenylamine having one to two sulfonamido groups in positions ortho to the —NH— moiety separating the two phenyl groups of the para-sulfonamidodiphenylamine and wherein the para-sulfonamidodiphenylamine, in oxidized form, intramolecularly reacts to produce a sulfonamido substituted phenazine dye, said process comprising the step of:
   developing said element by means of a 3-pyrazolidone cross-oxidizing silver halide developing agent.

28. A method of producing a phenazine dye enhanced silver image in an exposed photographic element comprising a support having thereon a photographic silver salt and a phenazine dye precursor consisting essentially of a color-forming para-sulfonamidodiphenylamine represented by the formula:

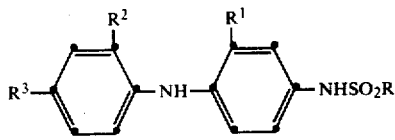

wherein:
R is alkyl containing 1 to 20 carbon atoms, aryl containing 6 to 20 carbon atoms, or alkaryl containing 7 to 20 carbon atoms;
$R^1$ and $R^2$ are individually hydrogen, alkyl containing 1 to 4 carbon atoms or —$NHSO_2R^4$; and at least one of $R^1$ and $R^2$ is —$NHSO_2R^4$;
$R^3$ is alkoxy containing 1 to 20 carbon atoms, alkyl containing 1 to 20 carbon atoms, or

$R^4$ is alkyl containing 1 to 20 carbon atoms or aryl containing 6 to 20 carbon atoms;
$R^5$ is hydrogen or alkyl containing 1 to 20 carbon atoms; and
$R^6$ is alkyl containing 1 to 20 carbon atoms; and, wherein the para-sulfonamidodiphenylamine has one to two sulfonamido groups in positions ortho to the —NH— moiety separating the two phenyl groups of the para-sulfonamidodiphenylamine; and, wherein the para-sulfonamidodiphenylamine, in oxidized form, intramolecularly reacts to produce a sulfonamido substituted phenazine dye; said process comprising the step of:
   developing said element by means of a 3-pyrazolidone cross-oxidizing silver halide developing agent.

29. A method of producing a phenazine dye enhanced silver image in an exposed photographic element comprising, in a gelatino binder, in reactive association, photographic silver halide and a sulfonamidodiphenylamine represented by the formula:

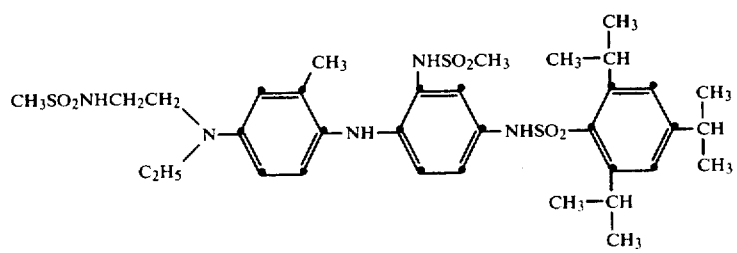

said process comprising the step of:
developing said phenazine dye enhanced silver image by means of a 3-pyrazolidone cross-oxidizing silver halide developing agent.

30. In a photographic silver halide processing composition for producing a dye enhanced silver image comprising:
(a) a cross-oxidizing photographic silver halide developing agent, and
(b) a color-forming dye precursor,
the improvement comprising:
as said dye precursor, a para-sulfonamidodiphenylamine having one to two sulfonamido groups in positions ortho to the —NH— moiety separating the two phenyl groups of the para-sulfonamidodiphenylamine and wherein the para-sulfonamidodiphenylamine, in oxidized form, intramolecularly reacts to produce a sulfonamido substituted phenazine dye.

31. A photographic silver halide processing composition as in claim 30 also comprising a base or base-release agent.

32. A photographic silver halide processing composition as in claim 30 wherein said dye precursor comprises a para-sulfonamidodiphenylamine represented by the formula:

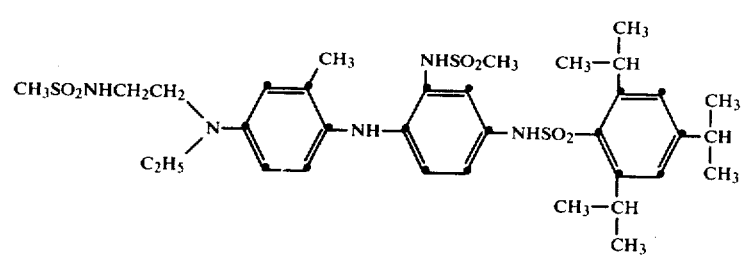

33. An exposed and processed photographic element comprising a support having thereon a silver image and a phenazine dye image comprising a phenazine dye represented by the formula:

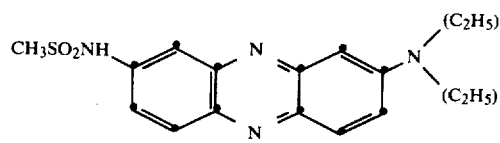

wherein:
R$^7$ is alkyl containing 1 to 20 carbon atoms, aryl containing 6 to 20 carbon atoms, or alkaryl containing 7 to 20 carbon atoms;
R$^8$ is alkoxy containing 1 to 20 carbon atoms, alkyl containing 1 to 20 carbon atoms, or

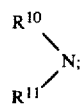

R$^9$ is hydrogen, alkyl containing 1 to 4 carbon atoms or —NHSO$_2$R$^{12}$;
R$^{10}$ is hydrogen or alkyl containing 1 to 20 carbon atoms;
R$^{11}$ is alkyl containing 1 to 20 carbon atoms; and
R$^{12}$ is alkyl containing 1 to 20 carbon atoms, aryl containing 6 to 20 carbon atoms or alkaryl containing 7 to 20 carbon atoms.

34. An exposed and processed photographic element as in claim 33 also comprising a binder and wherein said silver image consists essentially of a silver image.

35. An exposed and processed photographic element comprising a support having thereon, in binder, a silver image enhanced by a phenazine dye image comprising a phenazine dye represented by the formula:

36. An exposed and processed photographic element comprising a support having thereon, in binder, a silver image enhanced by a phenazine dye image comprising a phenazine dye represented by the formula:

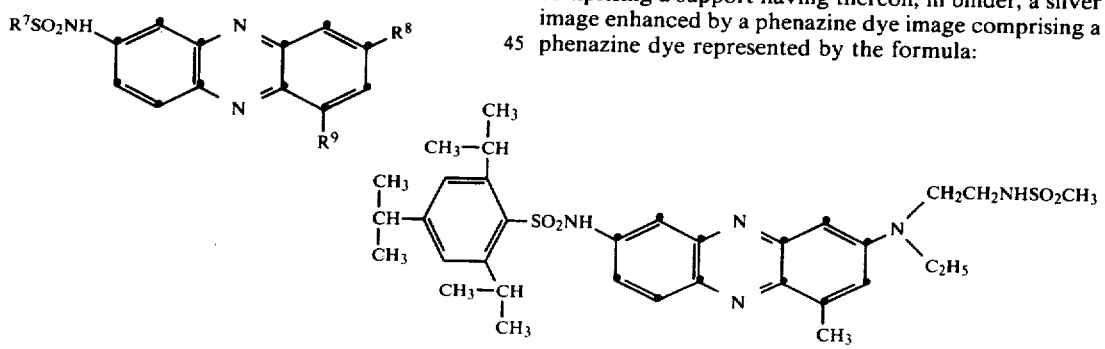

37. An exposed and processed photographic element comprising a support having thereon, in binder, a silver image enhanced by a phenazine dye image comprising a phenazine dye represented by the formula:

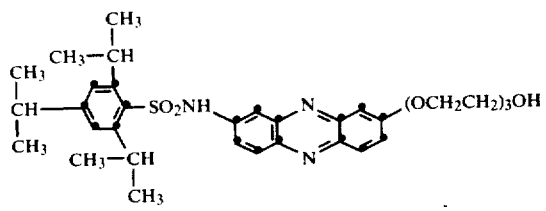

38. An exposed and processed photographic element comprising a support having thereon, in binder, a silver image enhanced by a phenazine dye image comprising a phenazine dye represented by the formula:

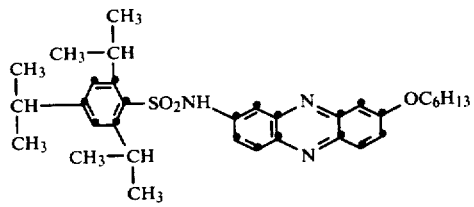

39. An exposed and processed photographic composition comprising, in binder, a silver image and a phenazine dye image comprising a phenazine dye represented by the formula:

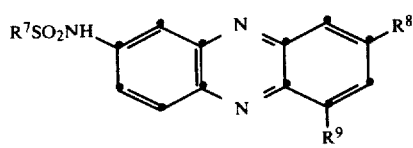

wherein:
R$^7$ is alkyl containing 1 to 20 carbon atoms, aryl containing 6 to 20 carbon atoms, or alkaryl containing 7 to 20 carbon atoms;
R$^8$ is alkoxy containing 1 to 20 carbon atoms, alkyl containing 1 to 20 carbon atoms, or

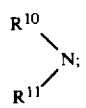

R$^9$ is hydrogen or alkyl containing 1 to 4 carbon atoms;
R$^{10}$ is hydrogen or alkyl containing 1 to 20 carbon atoms;
R$^{11}$ is alkyl containing 1 to 20 carbon atoms; and
R$^{12}$ is alkyl containing 1 to 20 carbon atoms, aryl containing 6 to 20 carbon atoms or alkaryl containing 7 to 20 carbon atoms.

40. An exposed and processed photographic composition comprising, in binder, a silver image enhanced by a phenazine dye image comprising a phenazine dye represented by the formula:

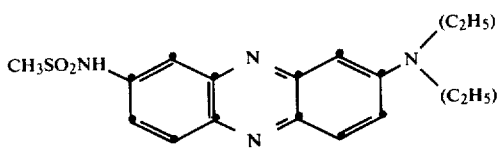

41. An exposed and processed photographic composition comprising, in binder, a silver image enhanced by a phenazine dye image comprising a phenazine dye represented by the formula:

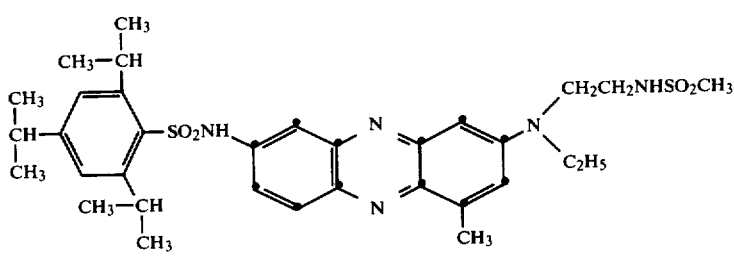

42. An exposed and processed photographic composition comprising, in binder, a silver image enhanced by a phenazine dye image comprising a phenazine dye represented by the formula:

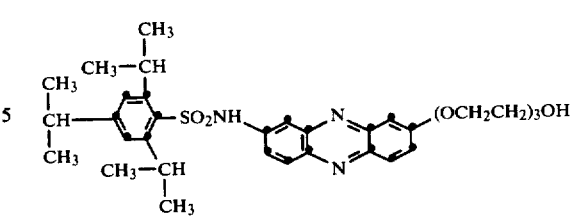

43. An exposed and processed photographic composition comprising, in binder, a silver image enhanced by a phenazine dye image comprising a phenazine dye represented by the formula:

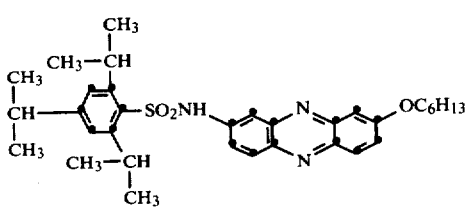

44. An exposed and processed photographic composition comprising, in binder, a silver image enhanced by a phenazine dye image comprising a phenazine dye represented by the formula:

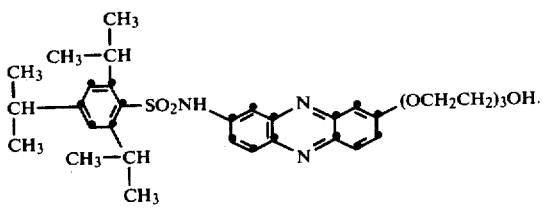

* * * * *